US010685748B1

(12) United States Patent
Chappell et al.

(10) Patent No.: US 10,685,748 B1
(45) Date of Patent: Jun. 16, 2020

(54) SYSTEMS AND METHODS FOR SECURE PROCESSING OF EYE TRACKING DATA (71) Applicant: EyeTech Digital Systems, Inc., Mesa, AZ (US)

(72) Inventors: Robert C Chappell, Mesa, AZ (US); Miles Manning, Gilbert, AZ (US); Sonal Kalbande, Tempe, AZ (US)

(73) Assignee: EyeTech Digital Systems, Inc., Mesa, AZ (US)

( * ) Notice: Subject to any disclaimer, the term of this patent is extended or adjusted under 35 U.S.C. 154(b) by 0 days.

(21) Appl. No.: 16/788,770

(22) Filed: Feb. 12, 2020

(51) Int. Cl.
*G16H 50/20* (2018.01)
*G06F 21/62* (2013.01)
*G16H 10/20* (2018.01)
*G06Q 10/10* (2012.01)
*G06N 20/00* (2019.01)
*G06N 5/04* (2006.01)
(Continued)

(52) U.S. Cl.
CPC .............. *G16H 50/20* (2018.01); *G06F 3/013* (2013.01); *G06F 21/6245* (2013.01); *G06N 5/04* (2013.01); *G06N 20/00* (2019.01); *G06Q 10/10* (2013.01); *G16H 10/20* (2018.01); *G16H 10/60* (2018.01); *G06F 2221/2107* (2013.01); *G06Q 2220/00* (2013.01)

(58) Field of Classification Search
CPC ... A61B 8/0808; A61B 5/7264; A61B 5/0013; A61B 5/0261; A61B 5/6803; A61B 5/4082; A61B 5/742; A61B 3/113; A61B 5/4076; A61B 5/1128; A61B 5/4088; A61B 5/163; A61B 5/1176; A61B 5/1114; G16H 50/20; G16H 40/67; G16H 15/00; G16H 80/00; G16H 40/63; G16H 50/30; G16H 10/60; G16H 50/70; G16H 10/00; G16H 40/60; G06F 19/00; G06F 19/321; G06F 19/3418
See application file for complete search history.

(56) References Cited

U.S. PATENT DOCUMENTS 5,367,315 A  11/1994  Pan
7,572,008 B2  8/2009  Elvesjo
8,350,889 B1  1/2013  Shammoh
(Continued)

OTHER PUBLICATIONS

U.S. Appl. No. 16/434,830, filed Jun. 7, 2019; Robert C. Chappell et al. "Devices and Methods for Reducing Computational and Transmission Latencies in Cloud Base Eye Tracking Systems".

*Primary Examiner* — Joseph D Burgess
(74) *Attorney, Agent, or Firm* — Jennings Strouss & Salmon PLC; Michael K. Kelly; Daniel R. Pote (57) ABSTRACT

Systems and methods are provided for processing and storing eye-tracking data. A visual stimulus is provided to an experimental subject on a display. Eye-tracking data associated with the behavior of the experimental subject is acquired and stored while observing the visual stimulus on the display. The eye-tracking data is stored as primary data and secondary data, wherein the primary data is stored in an encrypted form using a secret key associated with the experimental subject. In response to a research request, the secondary data is transmitted for storage in a research database and, in response to a second research request authorized by the experimental subject, the primary data is transmitted for storage in the research database subsequent to decrypting the primary data using the secret key.

5 Claims, 4 Drawing Sheets

(51) Int. Cl.
 *G06F 3/01* (2006.01)
 *G16H 10/60* (2018.01)

(56) References Cited

U.S. PATENT DOCUMENTS

| | | |
|---|---|---|
| 2014/0225131 A1 | 8/2014 | Benson et al. |
| 2015/0223684 A1 | 8/2015 | Hinton |
| 2015/0227735 A1 | 8/2015 | Chappell |
| 2016/0106315 A1* | 4/2016 | Kempinski ............ A61B 3/113 351/210 |
| 2016/0262685 A1* | 9/2016 | Wagner ................ A61B 5/1101 |
| 2017/0068287 A1 | 3/2017 | Jung et al. |
| 2018/0307270 A1 | 10/2018 | Pantel |
| 2019/0312973 A1 | 10/2019 | Engelke et al. |

* cited by examiner

SYSTEMS AND METHODS FOR SECURE PROCESSING OF EYE TRACKING DATA

TECHNICAL FIELD

The present invention relates, generally, to eye-tracking systems and methods and, more particularly, to the secure processing, storage, and delivery of data, such as medical-related data, generated by such eye-tracking systems.

BACKGROUND

Eye-tracking systems—such as those used in conjunction with desktop computers, laptops, tablets, virtual reality headsets, and other computing devices that include a display—generally include one or more illuminators configured to direct infrared light to the user's eyes and an image sensor that captures the images for further processing. By determining the relative locations of the user's pupils and the corneal reflections produced by the illuminators, the eye-tracking system can accurately predict the user's gaze point on the display.

In addition to increasing the usability of computing devices, it has also been confirmed that the behavior of an individual's eyes can be linked to cognitive processes, such as attention, memory, and decision-making. Accordingly, changes in eye movements over time may accompany and help predict the changes that occur in the brain due to aging and neurodegeneration. Such changes may thus be early leading indicators of Alzheimer's disease, Parkinson's disease, and the like.

While it would be advantageous to collect eye tracking data and images of a user's face to perform empirical testing for medical purposes, it is difficult to do so as a result of the regulatory scheme associated with the privacy and security of such data (see, e.g., HIPPA). There is therefore a long-felt need for secure systems and methods for processing and storing eye-gaze data to be used in connection with clinical trials and medical diagnoses. Systems and methods are therefore needed that overcome these and other limitations of the prior art.

SUMMARY OF THE INVENTION

Various embodiments of the present invention relate to systems and methods for, inter alia: i) a protocol for processing and storing eye-tracking data in a secure manner; ii) the use of such eye-tracking data to diagnose medical conditions and performing empirical research; iii) providing access to such eye-tracking data to clinical researchers in a secure manner; and iv) the use of machine learning and predictive analytics models in connection with such eye-tracking data to diagnose medical conditions.

BRIEF DESCRIPTION OF THE DRAWING FIGURES

The present invention will hereinafter be described in conjunction with the appended drawing figures, wherein like numerals denote like elements, and.

DETAILED DESCRIPTION OF PREFERRED EXEMPLARY EMBODIMENTS

The present subject matter relates to improved systems and methods for securely processing and storing eye-tracking data and providing such data for use by researchers to diagnose medical conditions. In that regard, the following detailed description is merely exemplary in nature and is not intended to limit the inventions or the application and uses of the inventions described herein. Furthermore, there is no intention to be bound by any theory presented in the preceding background or the following detailed description. In the interest of brevity, conventional techniques and components related to eye-tracking algorithms, image sensors, machine learning systems, cognitive diseases, encryption schemes, and digital image processing may not be described in detail herein.

Figure 1:
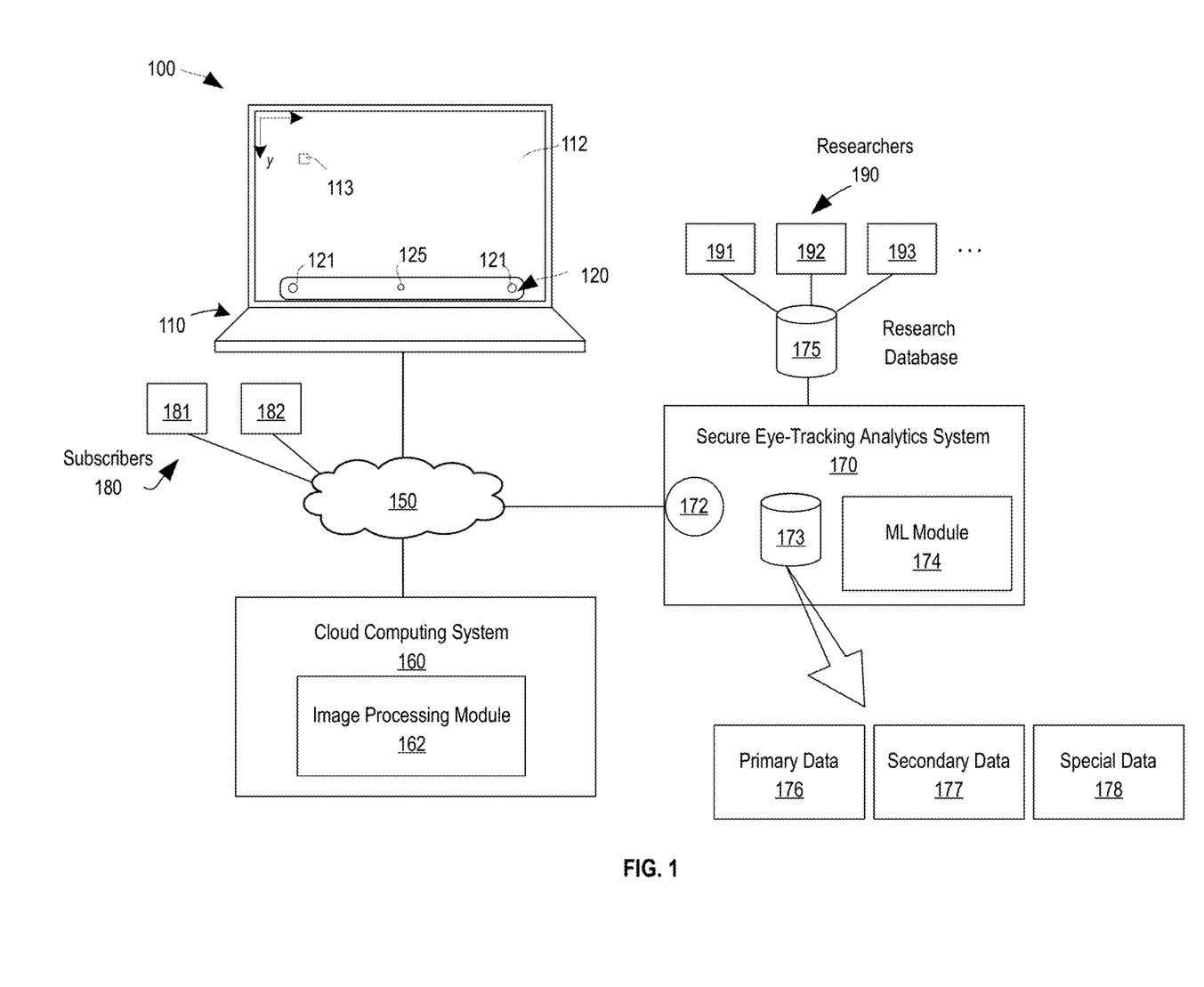
FIG. 1 is a conceptual block diagram illustrating a secure eye-tracking system in accordance with various embodiments.
Figure 2:
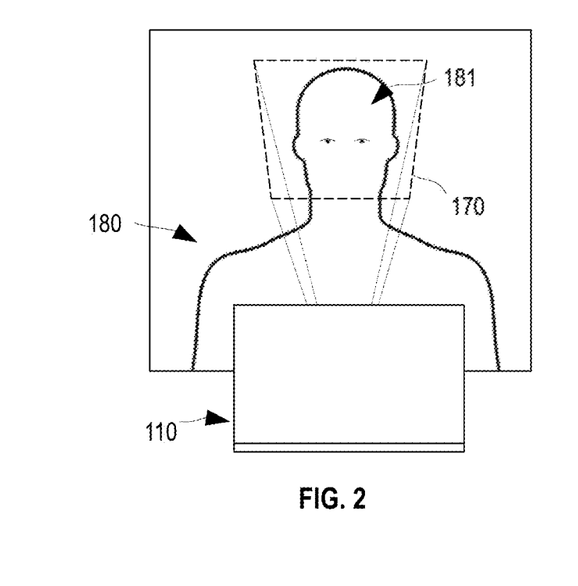
FIGS. 2 and 3A-3B illustrate the determination of eye-tracking data in accordance with various embodiments.

Referring first to FIG. 1 in conjunction with FIG. 2, the present invention is generally implemented in the context of a system 100 that includes some form of computing device 110 (e.g., a desktop computer, tablet computer, laptop, smart-phone, head-mounted display, television panels, dashboard-mounted automotive systems, or the like) having an eye-tracking assembly 120 coupled to, integrated into, or otherwise associated with device 110. The eye-tracking assembly 120 is configured to observe the facial region 181 of a user (alternatively referred to as a "patient" or "experimental subject") within a field of view 170 and, through various techniques described in detail below, track the location and movement of the user's gaze (or "gaze point") 113 on a display (or "screen") 112 of computing device 110. The gaze point 113 may be characterized, for example, by a tuple (x, y) specifying linear coordinates (in pixels, centimeters, or other suitable unit) relative to an arbitrary reference point on display screen 112 (e.g., the upper left corner, as shown).

In the illustrated embodiment, eye-tracking assembly 120 includes one or more infrared (IR) light emitting diodes (LEDs) 121 positioned to illuminate facial region 181 of user 180. Assembly 120 further includes one or more cameras 125 configured to acquire, at a suitable frame-rate, digital images corresponding to region 181 of the user's face.

Figure 3A:
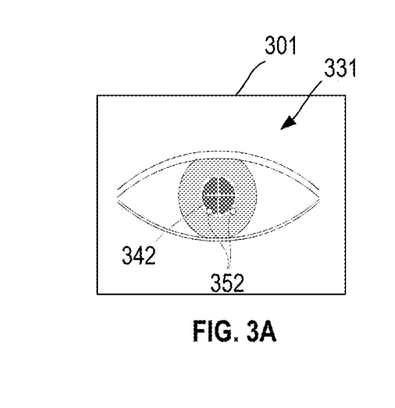
Figure 3B:
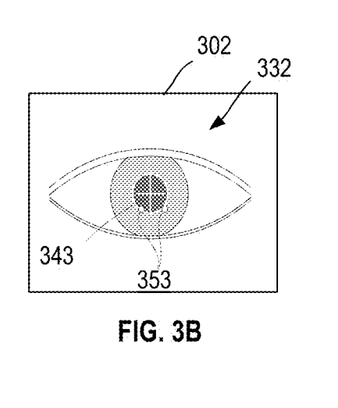

Referring to FIGS. 3A and 3B in conjunction with FIGS. 1 and 2, the eye-tracking system 100 acquires an image of the user's facial region 181 and determines the location within that image of the user's eyes. The system 100 then determines the pupil centers (PCs) and corneal reflections (CRs) for each eye. Referring to FIGS. 3A and 3B, for example, the system may process a first image 301 including a first eye 331 (e.g., the user's right eye) having a PC 342 and CRs 352, and a second image 302 including a second eye 332 (e.g., a left eye) having a PC 343 and CRs 353.

The system 100 then processes the PC and CR data, as well as information regarding the position and orientation of the user's head, and produces gaze data, which in one embodiment includes the gaze coordinates (x, y) (113 in FIG. 1) along with other optional information, such as a value specifying the user's distance from eye tracking assembly 120.

In some embodiments, the image data may be processed locally (i.e., within computing device 110) using an installed software client to determine gaze point 113. In some embodiments, however, eye tracking is accomplished using an image processing module or modules 162 that that are remote from computing device 110—e.g., hosted within a cloud computing system 160 communicatively coupled to computing device 110 over a network 150 (e.g., the Internet). In such embodiments, image processing module 162 performs the computationally complex operations necessary to determine the gaze point and is then transmitted back (as eye and gaze data) over the network to computing device 110. An example cloud-based eye-tracking system that may employed in the context of the present invention may be found, for example, in U.S. patent application Ser. No. 16/434,830, entitled "Devices and Methods for Reducing Computational and Transmission Latencies in Cloud Based Eye Tracking Systems," filed Jun. 7, 2019, the contents of which are hereby incorporated by reference.

System 100 further includes a secure eye-tracking analytics system (or simply "analytics system") 170 communicatively coupled to cloud computing system 160 and/or computing device 110 via a network 150 (e.g., the Internet). System 170 itself includes a data processing module 172, a database (or data store) 173, and a machine learning (ML) module 174.

As a preliminary matter, the phrase "machine learning" model is used without loss of generality to refer to any result of an analysis method that is designed to make some form of prediction, such as predicting the state of a response variable, clustering patients, determining association rules, and performing anomaly detection. Thus, for example, the term "machine learning" refers to models that undergo supervised, unsupervised, semi-supervised, and/or reinforcement learning. Such models may perform classification (e.g., binary or multiclass classification), regression, clustering, dimensionality reduction, and/or such tasks. Examples of such models include, without limitation, artificial neural networks (ANN) (such as a recurrent neural networks (RNN) and convolutional neural network (CNN)), decision tree models (such as classification and regression trees (CART)), ensemble learning models (such as boosting, bootstrapped aggregation, gradient boosting machines, and random forests), Bayesian network models (e.g., naive Bayes), principal component analysis (PCA), support vector machines (SVM), clustering models (such as K-nearest-neighbor, K-means, expectation maximization, hierarchical clustering, etc.), linear discriminant analysis models.

A research database or set of databases 175 are selectively provided to one or more researchers 190 (e.g., researchers 191-193) who, as detailed below, are able to interrogate and otherwise use the eye-tracking data stored in database 182 for the purpose of performing medical-related research. The data provided to researchers 190 via database 175 will generally be a subset of the data stored within the main database 173, as described in detail below, and is preferably stored in a secure manner and protected using an appropriate authentication and authorization process.

ML module 174 is configured to train, test, and validate machine learning models and otherwise perform predictive analytics (under the direction of a researcher 190) based on the eye-tracking data securely stored within database 175. Any suitable machine learning or predictive analytics platform and/or software libraries may be used to generate these models, as is known in the art. In some embodiments, answers to the questionnaire previously provided to the patient(s) are used to train the machine learning model (i.e., in addition to available eye-tracking data).

The various components of FIG. 1 may be implemented using a variety of available platforms, and is not limited to any particular architecture. For example, system 100 may be deployed on Microsoft Azure, Google Cloud Platform, or Amazon Web Services (AWS).

In some embodiments, when a researcher 190 determines that a certain model has particular efficacy—e.g., in predicting the onset of some form of cognitive impairment—that model may be transferred to or otherwise implemented within ML Module 174 such that the model is accessible via one or more "subscribers" 180 (e.g., 181 and 182) who can then use the trained model in connection with individual patients (e.g., to determine the likelihood that a particular patient has the specified impairment).

While researchers 190 and subscribers 180 are shown as two separate types of entities in FIG. 1, these designations actually correspond to two separate roles, which may be applicable to the same individual or entity. For example, a researcher 191 might be provided access to certain eye-tracking data to test a hypothesis that a certain pattern of microsaccades is correlated to an increased chance of Alzheimer's disease. Testing may confirm that a particular predictive analytics model can assist in this diagnoses. That predictive analytics model (trained, validated, and tested on the data within database 175) may then be implemented within ML module 174 and provided to subscribers (including, in this example, original researcher 191) who can then use that model for prediction by feeding it new data generated by patients subsequently using the same or different eye-tracking system 120.

The phrase "eye-tracking data" may be used herein to refer to any data or information directly or indirectly derived from an eye-tracking session. As shown in FIG. 1, however, this data may be categorized, generally, by the likelihood that such data may be tracked back to a particular user (e.g., personally identifiable information, or PII).

In the illustrated embodiment, for example, the data stored within database 173 is segmented into primary data 176, secondary data 177, and special data 178. Primary data 176 generally includes actual images of a user's facial region, as previously described. Such data would typically be subject to a strong level of security—i.e., stored in an encrypted form using a secret key (e.g., a password, certificate, or the like), which may be stored in system 170 and only accessible to the administrators of that system.

A variety of symmetrical and/or asymmetrical encryption schemes and standards may be employed to securely handle the eye-tracking data at rest (e.g., in database 173) and in motion (e.g., when being transferred between the various modules illustrated in FIG. 1). Without limiting the foregoing, such encryption standards and key-exchange protocols might include Triple Data Encryption Standard (3DES), Advanced Encryption Standard (AES) (such as AES-128, 192, or 256), Rivest-Shamir-Adelman (RSA), Twofish, RC4, RC5, RC6, Transport Layer Security (TLS), Diffie-Hellman key exchange, and Secure Sockets Layer (SSL). In addition, various hashing functions may be used to address integrity concerns associated with the eye-tracking data.

Secondary data 177 includes numeric and/or categorical data derived from primary data 181, such as gaze point coordinates, corneal reflection and pupil center data, saccade (and micro-saccade) information, and non-image frame data. More generally, the secondary data 177 might include information regarding fixations (phases when the eyes are stationary between movements), saccades (rapid and involuntary eye movements that occur between fixations) scan-path (series of short fixations and saccades alternating before the eyes reach a target location on the screen), duration (sum of all fixations made in an area of interest), and blink (quick, temporary closing of eyelids), and pupil size (which might correlate to cognitive workload, etc.).

Special data 178 includes additional sensitive information that might be subject to particular regulatory control, such as medical information, academic (grade) information, or information relating to children. Such data may be governed, for example, by HIPPA, FERPA, and COPPA regulations, respectively. Such data might also be characterized as either primary data or secondary data in some contexts, but will generally be subject to particular administrative, physical, and technical security measures.

In one embodiment, secondary data 177 is provided to researchers 190 in database 175 with its Experimental ID encrypted. In the event that a researcher 190 requires primary data 176 (e.g., face images), then the researcher 190 will make a request (to the administrator or other controller of system 170) based on the encrypted Experiment ID and a Record ID. System 170 will have access to the decryption key for Experiment ID, and this Experiment ID will be used to determine (via decryption) which user the secondary data belongs to. The system in turn reaches out to that user, requesting access to the images.

Figure 4:
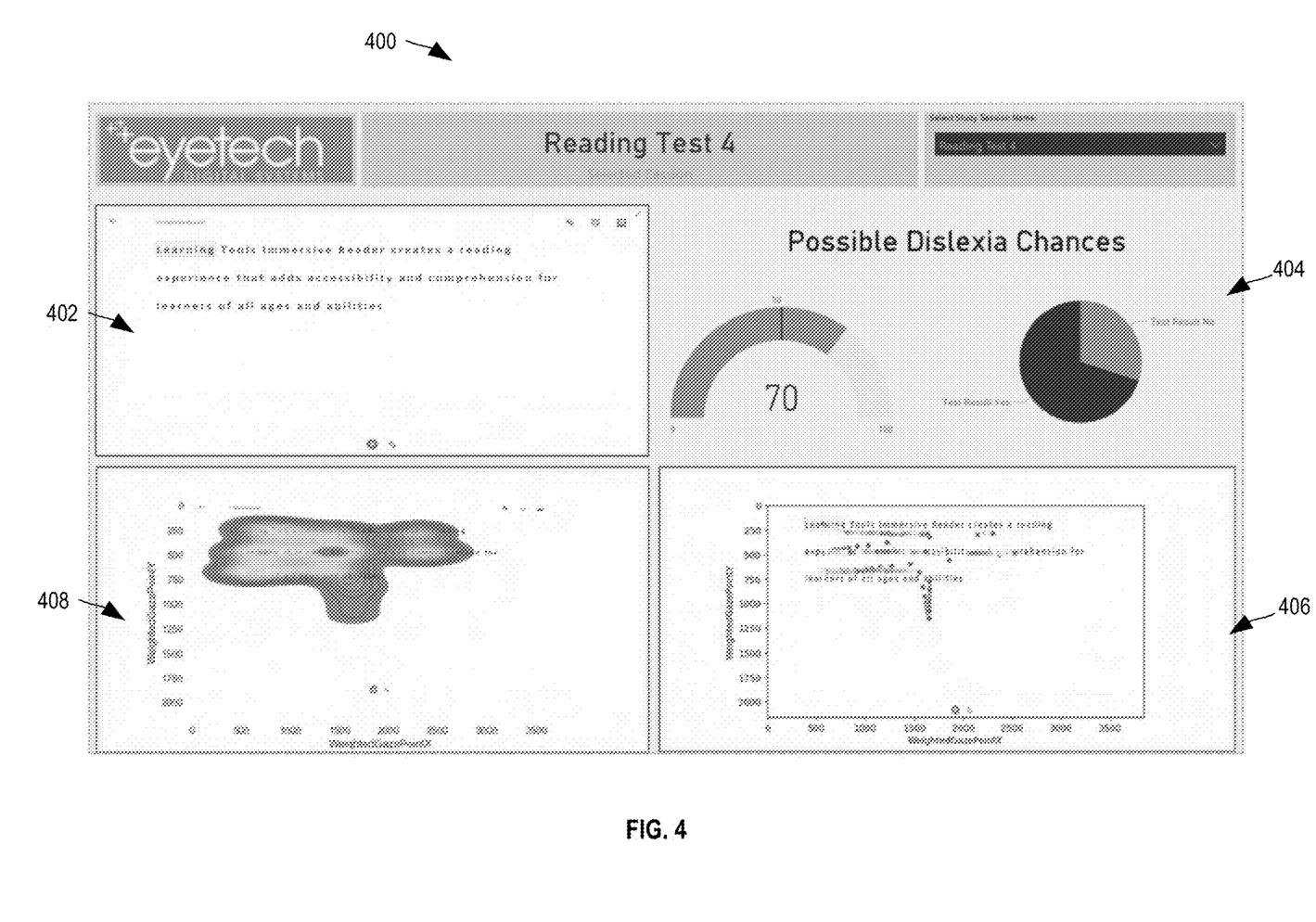
FIG. 4 illustrates a dashboard user interface in accordance with an exemplary embodiment.

FIG. 4 illustrates an example "dashboard"—i.e., a user interface that provides results, analytics, visualizations, and other information relating to an experiment performed using the stored eye-tracking data. Researchers 190 and/or subscribers 180 may be provided access to this dashboard. The purpose of dashboard 400 is to present the researcher (or other individual with access to system 100) with information relevant to an experiment that has been performed on the stored eye-tracking data and/or a predictive analytics model resulting from an experiment.

In that regard, FIG. 4 is presented as just one example, and is not meant to be limiting. In the illustrated embodiment, for example, dashboard 400 includes a stimulus text section 402 corresponding to a stream of text that was previously presented to the patient during an experiment. Dashboard 400 also includes a hot-spot diagram 408 graphically illustrating the duration that a user's eyes were directed to corresponding points in text section 402. Dashboard 400 may also include a mapping 406 of eye gaze data points associated with the user's eye-gaze information for text section 402. A prediction region 404 may then be used to summarize the result of applying the eye-tracking data to the previously trained machine learning model. A variety of stimuli may be provided to the patient during the experiment, including without limitation text to read, an animation to observe, simple stationary images, and/or videos for the subject to watch.

Figure 5:
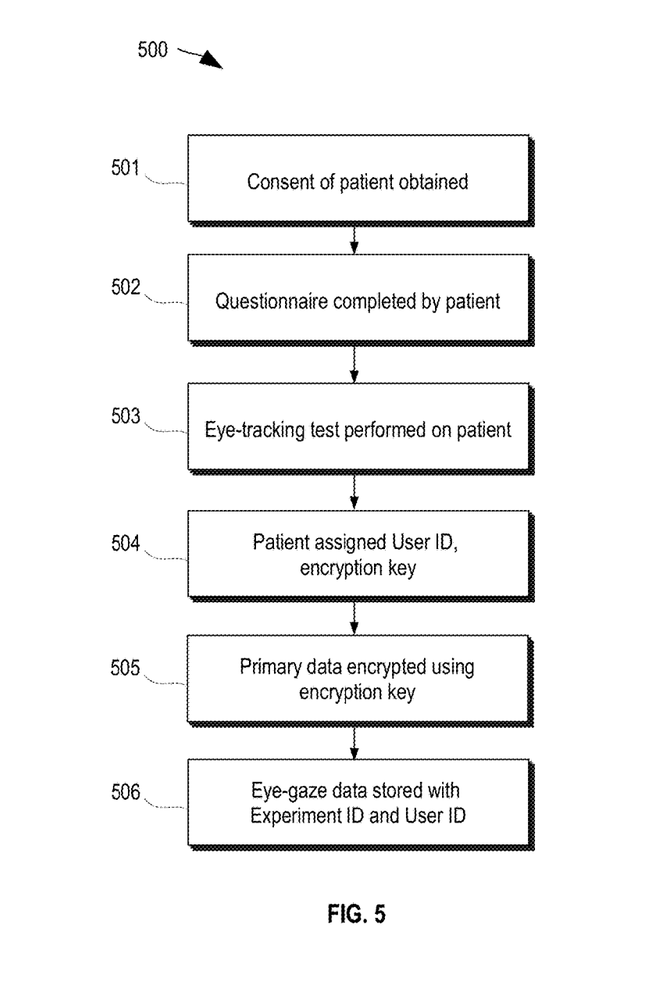
FIG. 5 is a flowchart illustrating a user-centric use-case in accordance with one embodiment.

Having thus given an overview of a system in accordance with one embodiment, a method of operating such a system will now be described in conjunction with FIGS. 5 and 6. Specifically, FIG. 5 is a flowchart 500 illustrating a user-centric use-case in accordance with one embodiment. First, at 501, consent of the patient to undergo the test is obtained from the user (or "patient"). This may be accomplished through the execution of a written document or through an electronic means. Next, at 502, a questionnaire may be presented to, and completed by, the patient. Again, this step may be performed using either a paper or electronic format. The questionnaire might include questions regarding basic information (age, sex, diet, etc.), as well as specific information regarding cognitive processes. For example, on or more questions associated with the Informant IQCODE interview standard may be used. See, e.g., Harrison J. K., *Informant Questionnaire on Cognitive Decline in the Elderly (IQCODE) for the early diagnosis of dementia across a variety of healthcare settings*, Cochrane Database Syst. Rev. (2016), the contents of which are incorporated by reference.

Next, at 503, the actual eye-tracking test is performed by the patient. That is, the patient is presented with a graphic, video, or other stimulus, and the eye-tracking system (previously described) monitors the user's eyes and produces eye-tracking data (which will ultimately be stored in database 180). As noted previously, this data may include primary data 181, secondary data 182, and special data 183.

Next, at 504, the patient is assigned a secret encryption key (or password) that will be associated with a user ID assigned to the patient. In alternate embodiments, an asymmetrical (e.g., public key) encryption scheme is employed. Subsequently, at 505, a portion of the eye-tracking data is encrypted using the secret key. The data encrypted in this way may include, for example, the primary data 181 that might be considered PII. Subsequently, at 506, the eye-tracking data is stored along with its experiment ID and user ID in database 180, a portion of which may be encrypted as noted above. The patient's secret key may itself be stored in encrypted form within system 170.

Figure 6:
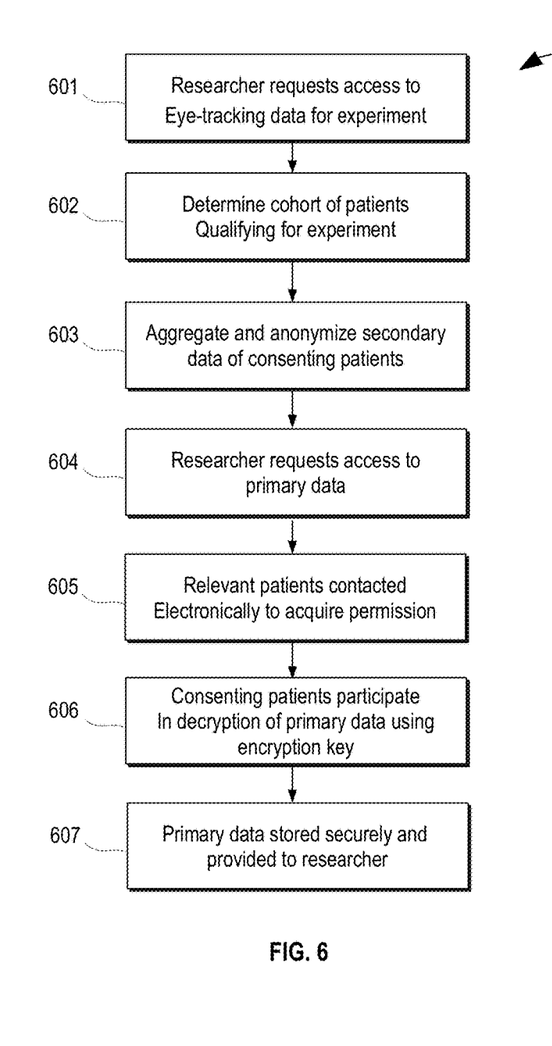
FIG. 6 is a flowchart illustrating a researcher-centric use-case in accordance with one embodiment.

FIG. 6 is a flowchart 600 illustrating a researcher-centric use-case in accordance with one embodiment. That is, as shown, the method begins with a researcher requesting access to a portion of the stored eye-tracking data 601, such as the secondary data 182 (which in most embodiments is not encrypted using the patient's secret key). Next, the system 100 determines, at 602, the cohort of patients that fit the requirements of the experiment being contemplated by the researcher. This may be determined using, for example, certain criteria specified by the researcher in combination with the questionnaire completed at step 502.

Next, at 603, the secondary data for those patients is aggregated and anonymized (or pseudonymized) and provided to the researcher (604). This might involve creating a separate, secure database that can be accessed by that researcher using appropriate authentication procedure, or may include providing the data to the researcher directly (e.g., in a secure format).

As mentioned above, there may be cases in which the researcher desires access to the primary data 181 (e.g., actual images of the patients face). In such cases, at step 605, the relevant patients are contacted electronically to acquire permission for the researcher to use such data. In the event that the patient does not grant permission, then that data is not provided. Otherwise, the secret keys of the consenting patients are used to decrypt that data (606). Subsequently, those images or other primary data are stored securely and provided to the researcher (607).

Summarizing, the methods in FIGS. 5 and 6 provide a framework that allows researchers to analyze and build models based on eye-gazing data in which non-sensitive information (e.g., the secondary data 182) is made available to the researcher, while more sensitive information (primary data 181) is only provided with permission of the patient and is otherwise encrypted using a secret key known only to the patient.

In summary, what have been described are various systems and methods for securely storing and processing eye-tracking data. The invention further contemplates the use of such eye-tracking data to diagnose medical conditions; providing access to such eye-tracking data to clinical researchers in a secure manner; and the use of machine learning models in connection with such eye-tracking data to diagnose medical conditions.

A secure eye-tracking data system in accordance with one embodiment includes a computing device configured to present, on a display, a visual stimulus to an experimental subject, and an eye-tracking system communicatively coupled to the computing device, the eye-tracking system configured to produce eye-tracking data associated with the behavior of the experimental subject during the presentation of the visual stimulus. The system further includes an eye-tracking analytics system configured to: (a) store the eye-tracking data as primary data and secondary data, wherein the primary data is stored in an encrypted form using a secret key provided by the experimental subject; (b) provide, in response to a research request, the secondary data for storage in a research database; (c) provide, in response to a second research request authorized by the experimental subject via the secret key, the primary data for storage in the research database.

In accordance with one embodiment, the eye-tracking analytics system is configured to implement a machine learning model previously trained using the stored eye-tracking data.

In accordance with one embodiment, the eye-tracking analytics system is further configured to provide, to a subscriber system, a dashboard user interface including a visual representation of the visual stimulus, a visual representation of the eye-tracking data, and a prediction resulting from applying the previously-trained machine learning model to eye-tracking data generated by the behavior of a second experimental subject during presentation of the visual stimulus.

In accordance with one embodiment, the primary data includes at least images of the experimental subject's face, and the secondary data includes at least eye-gaze coordinates.

In accordance with one embodiment, the research request includes criteria for selecting the eye-tracking data to be provided to the research database.

In accordance with one embodiment, the experimental subject is prompted to complete a digital questionnaire that is subsequently stored by the eye-tracking analytics system and selectively provided to the research database.

A method of processing and storing eye-tracking data in accordance with one embodiment includes presenting to an experimental subject, on a display of a computing device, a visual stimulus; acquiring storing eye-tracking data associated with the behavior of the experimental subject during the presentation of the visual stimulus; storing the eye-tracking data as primary data and secondary data, wherein the primary data is stored in an encrypted form using a secret key associated with the experimental subject; transmitting, in response to a research request, the secondary data for storage in a research database; and transmitting, in response to a second research request authorized by the experimental subject, the primary data for storage in the research database subsequent to decrypting the primary data using the secret key.

In accordance with one embodiment, the method includes implementing a machine learning model previously trained using the stored eye-tracking data.

In accordance with one embodiment, the method includes providing, to a subscriber system, a dashboard user interface that includes a visual representation of the visual stimulus, a visual representation of the eye-tracking data, and a prediction resulting from applying the previously-trained machine learning model to eye-tracking data generated by the behavior of a second experimental subject during presentation of the visual stimulus. In accordance with one embodiment, the primary data includes at least images of the experimental subject's face, and the secondary data includes at least eye-gaze coordinates. In some embodiments, the secondary data further includes micro-saccade data. In accordance with one embodiment, the research request is a digital form transmitted over a network and includes criteria for selecting the eye-tracking data to be provided to the research database.

In accordance with one embodiment, the experimental subject is prompted to complete a digital questionnaire that is subsequently stored by the eye-tracking analytics system and selectively provided to the research database.

Embodiments of the present disclosure may be described in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices.

In addition, those skilled in the art will appreciate that embodiments of the present disclosure may be practiced in conjunction with any number of systems, and that the systems described herein are merely exemplary embodiments of the present disclosure. Further, the connecting lines shown in the various figures contained herein are intended to represent example functional relationships and/or physical couplings between the various elements. It should be noted that many alternative or additional functional relationships or physical connections may be present in an embodiment of the present disclosure.

As used herein, the terms "module" or "controller" refer to any hardware, software, firmware, electronic control component, processing logic, and/or processor device, individually or in any combination, including without limitation: application specific integrated circuits (ASICs), field-programmable gate-arrays (FPGAs), dedicated neural network devices (e.g., Google Tensor Processing Units), electronic circuits, processors (shared, dedicated, or group) configured to execute one or more software or firmware programs, a combinational logic circuit, and/or other suitable components that provide the described functionality.

As used herein, the word "exemplary" means "serving as an example, instance, or illustration." Any implementation described herein as "exemplary" is not necessarily to be construed as preferred or advantageous over other implementations, nor is it intended to be construed as a model that must be literally duplicated.

While the foregoing detailed description will provide those skilled in the art with a convenient road map for implementing various embodiments of the invention, it should be appreciated that the particular embodiments described above are only examples, and are not intended to limit the scope, applicability, or configuration of the invention in any way. To the contrary, various changes may be made in the function and arrangement of elements described without departing from the scope of the invention.

The invention claimed is:

1. A method of securely processing and storing medical-related eye-tracking data, the method comprising:

presenting to an experimental subject, on a display of a computing device, a visual stimulus;

acquiring storing eye-tracking data associated with the behavior of the experimental subject during the presentation of the visual stimulus, wherein the eye-tracking data includes fixations data, saccade data, pupil-size data, and image data associated with the facial region and eyes of the experimental subject;

storing the image data as primary data and storing the fixations data, saccade data, and pupil-size data as secondary data, wherein the primary data is stored in an encrypted form using a secret key associated with the experimental subject;

transmitting, in response to a research request, the secondary data for storage in a research database;

transmitting, in response to a second research request authorized by the experimental subject, the primary data for storage in the research database subsequent to decrypting the primary data using the secret key;

implementing a machine learning model trained using the eye-tracking data stored in the research database to predict the likelihood of a patient having a neurogenerative disease; and providing, to a subscriber system, a dashboard user interface that includes a visual representation of the visual stimulus, a visual representation of the eye-tracking data, and a prediction resulting from applying the previously-trained machine learning model to eye-tracking data generated by the behavior of a second experimental subject during presentation of the visual stimulus.

2. The method of claim 1, wherein the secondary data includes micro-saccade data.

3. The method of claim 1, wherein the research request is a digital form transmitted over a network and includes criteria for selecting the eye-tracking data to be provided to the research database.

4. The method of claim 1, wherein the experimental subject is prompted to complete a digital questionnaire that is subsequently stored by the eye-tracking analytics system and selectively provided to the research database.

5. The method of claim 4, wherein the machine learning model additionally uses data derived from the completed digital questionnaire for training.

* * * * *